United States Patent [19]

Igaki

[11] Patent Number: 5,599,528
[45] Date of Patent: Feb. 4, 1997

[54] PREPARATION FOR EPIDERMIS

[75] Inventor: Takahisa Igaki, Chikushino, Japan

[73] Assignee: Sansho Seiyaku Co., Ltd., Onojo, Japan

[21] Appl. No.: 238,627

[22] Filed: May 5, 1994

[30] Foreign Application Priority Data

Sep. 30, 1993 [JP] Japan ..................... 5-244830

[51] Int. Cl.$^6$ ............... A61K 9/107; A61K 7/42; A61K 7/48
[52] U.S. Cl. ............... 424/59; 514/460; 514/782; 514/938; 514/975
[58] Field of Search ............... 514/460, 782, 514/938; 424/59

[56] References Cited

U.S. PATENT DOCUMENTS

| | | | |
|---|---|---|---|
| 4,536,519 | 8/1985 | Suzuki et al. | 514/785 |
| 4,788,001 | 11/1988 | Narua | 252/312 |
| 4,847,074 | 7/1989 | Hatae et al. | 514/460 |
| 4,919,921 | 4/1990 | Hatae | 514/460 |
| 4,948,577 | 8/1990 | Hara | 514/460 |
| 4,985,455 | 1/1991 | Motuno | 514/460 |
| 4,990,532 | 2/1991 | Yamamoto | 514/460 |
| 4,992,476 | 2/1991 | Geria I | 514/782 |
| 4,992,477 | 2/1991 | Geria II | 514/782 |
| 4,992,478 | 2/1991 | Geria III | 514/782 |
| 5,002,974 | 3/1991 | Geria IV | 514/782 |
| 5,216,033 | 6/1993 | Pereira et al. | 514/844 |
| 5,219,560 | 6/1993 | Suzuki et al. | 424/63 |
| 5,244,665 | 9/1993 | Natraj et al. | 424/401 |
| 5,304,334 | 4/1994 | Cahanas et al. | 252/314 |
| 5,378,455 | 1/1995 | Kealey et al. | 424/73 |

FOREIGN PATENT DOCUMENTS

| | | |
|---|---|---|
| 55-157509 | 12/1980 | Japan . |
| 55-154916 | 12/1980 | Japan . |
| 56-7776 | 1/1981 | Japan . |
| 56-77272 | 6/1981 | Japan . |
| 56-79616 | 6/1981 | Japan . |
| 59-33207 | 2/1984 | Japan . |
| 60-137253 | 7/1985 | Japan . |
| 60-146821 | 8/1985 | Japan . |
| 60-202806 | 10/1985 | Japan . |
| 61-109705 | 5/1986 | Japan . |
| 62-5909 | 1/1987 | Japan . |
| 62-108804 | 5/1987 | Japan . |
| 62-178506 | 8/1987 | Japan . |
| 62-198372 | 9/1987 | Japan . |
| 63-188609 | 8/1988 | Japan . |
| 1-83008 | 3/1989 | Japan . |
| 1-132502 | 5/1989 | Japan . |
| 2-28105 | 1/1990 | Japan . |
| 3-101609 | 4/1991 | Japan . |
| 3-193712 | 8/1991 | Japan . |
| 3-188011 | 8/1991 | Japan . |

OTHER PUBLICATIONS

Yamakawa CA. 116:200883 (and Derwent) of JPN 640/8010 (Jan. 22, 1992).
Sonozu GA: 116:180947 (and Derwent) of JPN 04009310 (Jan. 14, 1992).
Sansho Pharm (Derwent) of JPN 05213730 (Aug. 24, 1993).
Pola Kasei (Derwent) of JPN 62/088804 (May 20, 1987).

*Primary Examiner*—Shep K. Rose
*Attorney, Agent, or Firm*—Armstrong, Westerman, Hattori, McLeland & Naughton

[57] ABSTRACT

A preparation for epidermis containing kojic acid and/or its derivative and a surfactant or surfactants having HLB value adjusted to 12 or less than that is disclosed. This preparation is preferably in a form of O/W emulsion or W/O emulsion, with the latter being preferably formed by gel emulsification process. The surfactants or surface active agents serve to depress coloration or decomposition of kojic acid and/or its derivative and improve application feel of the preparation.

2 Claims, 3 Drawing Sheets

PREPARATION FOR EPIDERMIS

BACKGROUND OF THE INVENTION

This invention relates to a preparation for epidermis containing kojic acid and/or its derivative, in which kojic acid and/or its derivative is stable with time and which gives a pleasant feel upon application to the skin and, more particularly, to a preparation for epidermis containing kojic acid and/or its derivative, which further contains a surfactant having a specific HLB value. The surfactant serves to depress coloration or decomposition of kojic acid and/or its derivative and improve application feel of the preparation.

As typical forms of preparation for epidermis, there are illustrated O/W (oil-in-water) emulsions and W/O (water-in-oil) emulsions, which are different from each other in water-to-oil composition ratio and physical properties but are both homogeneous preparations wherein oil phase or aqueous phase are stably emulsified and dispersed with the aid of a surfactant.

O/W Emulsions and W/O emulsions are greatly different from each other in application feel and physical properties. That is, O/W emulsions well fit to the skin and are less sticky, thus providing favorable application feel, but spoil stability of water-soluble ingredients. Hence, O/W emulsions have problems in designing preparation form.

On the other hand, W/O emulsions provide excellent skin-protecting effect and ensure lasting effectiveness of the ingredient, but poorly fit to the skin and are more sticky. With respect to physical properties, W/O emulsions are liable to undergo oil phase separation at lower or higher temperatures, thus being difficult to obtain emulsion stability. Therefore, there has been required a large amount of surfactant or a stabilizing aid which, in turn, causes safety problem for skin.

Kojic acid and its derivatives the inventor has long studied are known as useful agents having various excellent properties, as disclosed in Japanese Unexamined Patent Publication No. S55-157509, Japanese Examined Patent Publication No. S56-18569, S58-22151, S58-22152, S58-34446, S60-7961, S60-9722 and S60-10005, Japanese Unexamined Patent Publication No. S60-137253, Japanese Examined Patent Publication No. S61-10447 and S61-60801, Japanese Unexamined Patent Publication No. S62-5909, Japanese Examined Patent Publication No. S62-3820 and S63-27322, Japanese Unexamined Patent Publication No. H1-132502 and Japanese Examined Patent Publication No. H5-30422.

However, kojic acid and its derivatives (hereinafter these being in some cases merely referred to as "kojic acids") are also known as agents which themselves have difficulty in acquiring stability. Particularly when the kojic acids are incorporated in the aforementioned O/W emulsion or W/O emulsion, it requires a highly sophisticated technique to design a proper formulation. Hence, it has been a pressing subject with respect to formation of a preparation containing the kojic acids to develop a technique which provides the kojic acids-containing prepatation with enough stability to stand severe distributive machinery without giving unpleasant feeling upon application thereof to skin.

In the case of compounding the kojic acids in O/W emulsions wherein kojic acid dissolves in the outer aqueous phase, they are under the condition of being likely to be exposed to ultraviolet light which can be an external cause of their coloration or decomposition. Thus, it has been conducted to compound an ultraviolet light absorbent in a proper amount for depressing damages by irradiation with ultraviolet light. Examples thereof are illustrated in, for example, Japanese Unexamined Patent Publication No. S62-108804 and S64-83008 and Japanese Examined Patent Publication No. H4-46924.

However, coloration of kojic acid is caused not only by irradiation with ultraviolet light but by heating and the like. Hence, the above-described techniques are still insufficient, and there have been attempted to use other stabilizing agents. Such techniques are described in, for example, Japanese Examined Patent Publication No. S63-24968 and H2-27963, Japanese Unexamined Patent Publication No. H3-101609, H3-188011 and H3-193712.

In the case of incorporating kojic acid in a W/O emulsion wherein kojic acid dissolves in the inner aqueous phase, coloration or decomposition of kojic acid due to ultraviolet light less takes place in comparison with an O/W emulsion. But, in some cases, kojic acid undergoes change with time due to mutual action with base ingredients. In order to depress such change, there have been used various specific additives as described in, for example, Japanese Unexamined Patent Publication No. H2-28105.

The above-described prior art is effective to some extent but fails to completely solve the problems.

Since both type emulsions still involve the problem of coloration or decomposition to varying degrees of kojic acid with time and the problem of not providing various choice of application feel, preparations of a formulation not containing large amounts of various stabilizing agents and yet being capable of stabilizing kojic acid and easily providing desired application feel have been desired.

SUMMARY OF THE INVENTION

It is, therefore, an object of the present invention to provide a preparation for epidermis which solves the above-described problems with the conventional O/W or W/O emulsion type preparations, i.e., which does not suffer coloration or decomposition of kojic acid or its derivative with time.

Other objects, features and advantages of the present invention will become apparent from the detailed description of the preferred embodiments of the invention to follow As a reslt of intensive investigations for solving the above-described problems, the inventor has found that a surfactant necessary in the O/W or W/O emulsion is one cause of spoiling stability of kojic acid. In the course of continuing investigations, the inventor has found that there exists some relation between HLB value of a surfactant and stability of kojic acid and that surfactants with a particular HLB value can solve the above-described problems, thus having completed the present invention.

That is, according to the present invention, there is provided a preparation for epidermis which contains kojic acid and/or its derivative and a surfactant having an HLB value adjusted to 12 or less. This preparation scarcely suffers coloration or decomposition with time of kojic acid and/or its derivative and gives a pleasant application feel.

DETAILED DESCRIPTION OF THE PREFERRED EMBODIMENTS OF THE INVENTION

Figure 1:
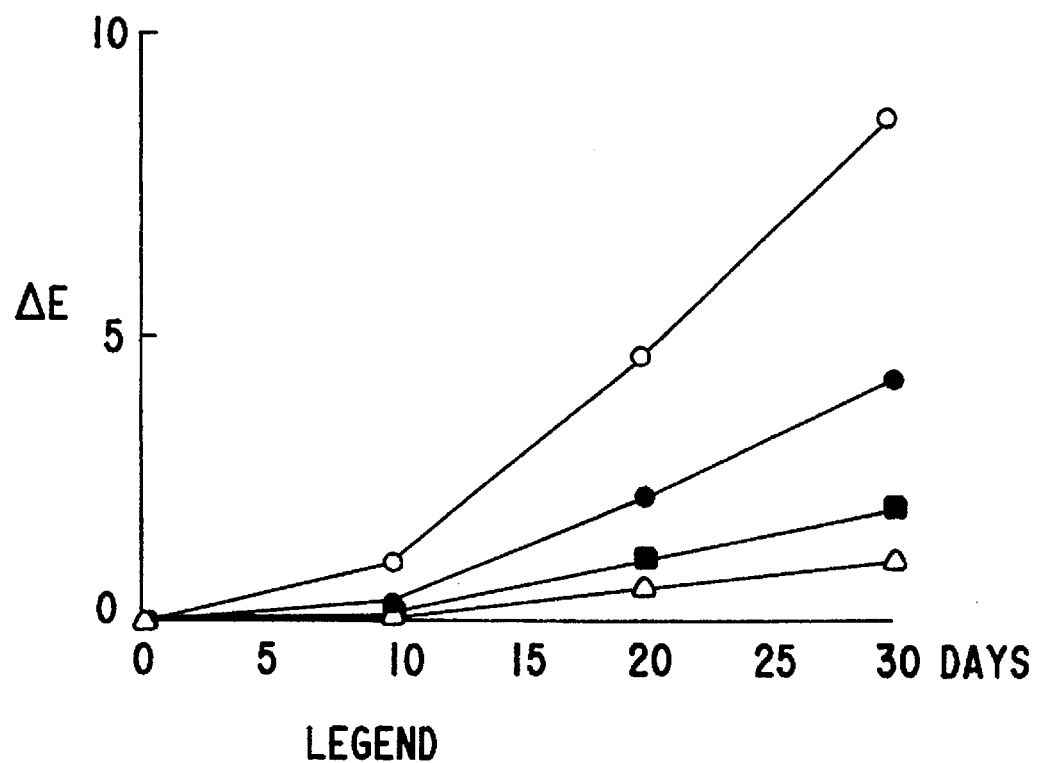
FIG. 1 is a graph showing change in coloration with time ($\Delta E$) at 45° C. of a simple lotion of 4.5 in pH containing 1% of kojic acid, with variously changing HLB value of a surfactant.

As the kojic acid (5-hydroxy-2-hydroxymethyl-γ-pyrrone), a pure product of 5-hydroxy-2-hydroxymethyl-γ-pyrrone, a fermentaion liquor containing kojic acid as a major component and being obtained by cultivating a known bacterium strain capable of yielding kojic acid, a concentrate of the fermentation liquor, a product obtained by extracting kojic acid from the fermentation liquor and crystallizing the extract, and the like.

As the kojic acid derivatives, those which are disclosed in, for example, Japanese Examined Patent Publication No. S60-10005, H1-45472 and H3-74229, and esterified products of kojic acid and kojic acid derivatives wherein sugars are bound to the —$CH_2OH$ group at 2-position of kojic acid disclosed in, for example, Japanese Examined Patent Publication No. S58-22151 and S58-22152 may be used alone or in combination of two or more. The term "kojic acid" includes these kojic acid derivatives.

The kojic acid and/or its derivative is compounded in the preparation in an amount of 0.001 to 10% by weight, preferably 0.1 to 5% by weight, based on the total amount of the preparation for external application.

HLB (Hydrophile-Lypophile-Balance) value represents a degree of balance between strength of hydrophilic group and that of lipophile group constituting a nonionic surfactant, and is determined by experiments. As calculation formulae for approximately calculating HLB value based on the structure of surfactant, there are known Griffin's formula and Kawakami's formula. In general, HLB values are considered as guides for designing a particular formulation, and the optimal balance between hydrophilicity and oleophilicity must be determined by experiments. In the present invention, this HLB value is used as a guide with respect to coloration of kojic acid as well as a guide for designing a stable formulation.

In the pressent invention, the term "surfactant having an HLB value adjusted to 12 or less preferably means a surfactant or a plurality of surfactants having 12 or less HLB value. Any of nonionic surfactants may be used alone or in combination of two or more. In addition, other type surfactants such as anionic surfactants, cationic surfactants and amphoteric surfactants may also be used in combination.

Further, nonionic surfactants having an HLB value of more than 12 may also be used by combining with a surfactant or surfactants having an HLB value of 12 or less so that the total surfactant mixture has an HLB value of 12 or less.

Additionally, HLB value of a mixture of x% of emulsion A having an HLB value of $HLB_A$ and (100−x)% emulsion B having an HLB value of $HLB_B$, i.e., $HLB_{AB}$, is approximately calculated as the arithmetrical mean according to the following formula, which has been confirmed by many experiments:

$$HLB_{AB}=HLB_A \cdot x/100+HLB_B \cdot (100-x)/100$$

As the surfactants to be used in the present invention having an HLB value of 12 or less, those nonionic surfactants which have a lower HLB value are particularly preferred. Examples and their HLB values (put in brackets) are illustrated below: sorbitan fatty acid esters such as sorbitan monolaurate [8.6], sorbitan monopalmitate [6.7], sorbitan monostearate [4.7], sorbitan sesquioleate [4.2], sorbitan tristearate [2.1], sorbitan monooleate [4.3], sorbitan sesquioleate [3.7], sorbitan trioleate [1.7], sorbitan monoisostearate [5.0] and sorbitan sesquiisostearate [4.5]; glycerol fatty acid esters such as glyceryl monomyristate [3.5], glyceryl monostearate [4.5], self-emulsifiable glyceryl monostearate [6.0], glyceryl monooleate [2.5] and glyceryl monoisostearate [4.0]; polyglycerol fatty acid esters such as diglyceryl monostearate [5.0], diglyceryl monooleate [5.5], diglyceryl dioleate [7.0], diglyceryl monoisostearate [5.5], tetraglyceryl monostearate [6.0], tetraglyceryl monooleate [6.0], hexaglyceryl monostearate [9.0], hexaglyceryl monooleate [9.0], hexaglyceryl tristearate [2.5], decaglyceryl tristearate [7.5], decaglyceryl trioleate [7.0], decaglyceryl triisostearate [7.0], decaglyceryl pentastearate [3.5], decaglyceryl triisostearate [7.0], decaglyceryl pentastearate [3.5], decaglyceryl pentaoleate [3.5] and decaglyceryl pentaisostearate [3.5]; polyoxyethylene sorbitol fatty acid esters such as polyoxyethylene (6) sorbitol hexastearate [3.0] and polyoxyethylene (6) sorbitol tetraoleate [8.5]; polyethylene glycol fatty acid esters such as polyethylene glycol (1 EO) monostearate [2.0], polyethylene glycol (2 EO) monostearate [4.0], polyethylene glycol (4 EO) monostearate [6.5], polyethylene glycol (2 EO) monooleate [4.5], polyethylene glycol (6 EO) monooleate [8.5], ethylene glycol monostearate [3.5], diethylene glycol stearate [4.5] and polyethylene glycol distearate [8.5]; polyoxyethylene alkyl ethers such as polyoxyethylene (2) cetyl ether [8.0], polyoxyethylene (2) stearyl ether [8.0], polyoxyethylene (4) stearyl ether [9.0], polyoxyethylene (2) oleyl ether [7.5] and polyoxyethylene (5) behenyl ether [7.0]; polyoxyethylene alkylphenyl ethers such as polyoxyethylene (2) nonylphenyl ether [4.5] and polyoxyethylene (3) octylphenyl ether [6.0]; polyoxyethylene castor oil hardened castor oil such as polyoxyethylene (3) castor oil [3.0], polyoxyethylene (10) castor oil [6.5], polyoxyethylene (5) hardened castor oil [6.0] and polyoxyethylene (10) hardened castor oil [6.5]; polyoxyethylene bees wax derivatives such as polyoxyethylene (6) sorbitol bees wax [7.5] and polyoxyethylene (20) sorbitol bees wax [9.5]; polyoxyethylene alkyl ether phosphates such as dipolyoxyethylene (2) alkyl ether phosphate [6.5], tripolyoxyethylene (2) alkyl ether phosphate [7.0], tripolyoxyethylene (6) alkyl ether phosphate [8.0] and dipolyoxyethylene (4) nonylphenyl ether phosphate [5.5]; propylene glycol fatty acid esters such as propylene glycol monostearate [3.5] and self-emulsifiable propylene glycol monostearate [4.0]; polyoxyethylene polyoxypropylene glycol ethers such as Poloxamer331 [4.5], Poloxamer401 [5.0], Poloxamer181 [5.8], Poloxamer182 [6.2], Poloxamer101 [7.0] and Poloxamer333 [9.0]; and sucrose fatty acid esters such as sucrose stearate [up to 1.0, 1.0, 2.0, 3.0, 5.0, 7.0, 9.0], sucrose palmitate [up to 1.0, about 1.0], sucrose oleate [about 1.0, 2.0] and sucrose laurate [about 1.0, 5.0]. These surfactants may preferably be used, but are not limitative at all.

As the surfactants having an HLB value of more than 12, there are illustrated polyglycerol fatty acid esters, polyoxyethylene sorbitan fatty acid esters, polyoxyethylene sorbitol fatty acid esters, polyethylene glycol fatty acid esters, polyoxyethylene castor oils, polyoxyethylene hardened castor oils, polyoxyethylene alkyl ethers, polyoxyethylene phytosterols, polyoxyethylene phytostanols, polyoxyethylene-polyoxypropylene alkyl ethers, polyoxyethylene alkylphenyl ethers, polyoxyethylene lanolins, polyoxyethylene lanolin alcohols, polyoxyethylene bees wax derivatives, polyoxyethylene alkylamines, polyoxyethylene fatty acid amides, polyoxyethylene polyoxypropylene glycol ethers, sucrose fatty acid esters, polyoxyethylene alkyl ether phosphates and the salts thereof.

Amounts of these surfactants vary depending upon the kinds but, usually, are 5 to 50% by weight, preferably 10 to 20% by weight, based on the total amount of the oil phase of the preparation.

A preparation for epidermis prepared in a known manner employing the technique of the present invention enable one to obtain a preferred application feel without spoiling stability of kojic acid and/or its derivative.

O/W emulsions, which can essentially give good feel upon application to skin, enable one to easily obtain desired application feel utilizing a thickening agent or a humectant as long as stability with time of kojic acid or its derivative.

W/O emulsions, which are inferior to O/W emulsions in the application feel due to their sticking properties, have been improved for removing such defects. As a result, W/O emulsions can be prepared by a recent emulsifying technique using a small amount of an oil phase ingredient. Typically, there is illustrated a gel emulsification process. Surprizingly enough, it has been found that an emulsion prepared according to the gel emulsification process gives improved application feel, and that stability of kojic acid or its derivative incorporated in the emulsion shows improved stability. The gel emulsification process is a process which comprises mixing an aqueous solution of polyhydric alcohol (e.g., 1,3-butylene glycol, glycerol, etc.) or sugar (e.g., sorbitol, maltitol, etc.) or amino acid (or its salt) into an oleophilic surfactant having a specific chemical structure to produce a gel wherein the surfactant forms the outer phase and the aqueous solution of polyhydric alcohol, sugar or amino acid (or its salt) forms the inner phase. When this gel is dispersed in an oil phase, followed by adding an aqueous phase thereto, there is obtained a quite characteristic stable W/O emulsion containing water in a wide range.

Of course, the thus prepared W/O preparation containing kojic acid has the characteristics essential to W/O emulsions. That is, when applied to the skin, the effective ingredient contained in the emulsion is not absorbed at once but is constantly absorbed over a certain period as is different from O/W preparations.

Further, the above-described techniques of the present invention relating to O/W emulsions and W/O emulsions can be applied to multi-layerd emulsions such as W/O/W emulsions and O/W/O emulsions to improve stability of kojic acid and/or its derivative incorporated therein. In addition, the present invention may also be applicable as a fundamental technique for microcapsule preparations.

The preparation of the present invention for epidermis is not particularly limited as to application form, and may be widely used in a known application form of medicines, quasi-drugs and cosmetics such as cataplasm, plaster, paste, cream, ointment, aerosol, emulsion, lotion, essence, pack, gel, powder, foundation, suncare, bath salts, and the like.

In forming the preparation of the present invention, various known and conventionally used effective ingredients may optionally be incorporated as the case demands in amounts not spoiling the objects of the present invention. Examples of such known effective ingredients include capillary vasodilators such as carpronium chloride, cepharanthine, vitamin E, vitamin E nicotinate, nicotinic acid, nicotinic acid amide, benzyl nicotinate, ginger tincture and chili tincture; coolers such as camphor, mentol and peppermint oil; antimicrobial agents such as hinokitiol, benzalkonium chloride and undecylenic acid; anti-inflammatory agents such as adrenal cortical hormone, aminocaproic acid, lysozyme chloride, glycyrrhizin and allantoin; fairness-imparting agents such as ascorbic acid and arbutin; various extracts of animal, vegetable or microbial origin such as placenta extract, liver extract, lithospermum root extract and extract of culture liquor of lactic acid bacteria.

In addition, the effects of the present invention may be enhanced by using a properly selected known ultraviolet light absorbent or a light-scattering agent.

Preferred examples thereof include benzophenone derivatives such as oxybenzone, oxybenzonesulfonic acid, sodium hydroxymethoxybenzophenonesulfonate and dihydroxydimethoxybenzophenone; salicylic acid derivatives such as ethylene glycol salicylate, homomenthyl salicylate and phenyl salicylate; urocanic acid and ethyl urocanate; cinnamic acid derivatives such as 2-ethylhexyl p-methoxycinnamate and octyl methoxycinnamate; p-aminobenzoic acid derivatives such as glyceryl p-aminobenzoate and 2-ethylhexyl p-dimethylaminobenzoate; dibenzoylmethane derivatives such as 4-tert-butyl-4'-methoxydibenzoylmethane; and benzotriazole derivatives such as 2-(2-hydroxy-5-methylphenyl)benzotriazole.

In addition to the known effective ingredients, various known additives such as humectants, antiseptics, antioxidants, chelating agents, pH-adjusting agents, perfumes and colorants may also be used, as well as a base ingredient such as a fat and oil, within a range of not spiling the objects of the present invention in the above-described application forms of medicines, quasi-drugs and cosmetics.

The present invention is now described in more detail by reference to experiments and formulations which, however, are not construed to be limitative at all.

EXPERIMENT 1

Test of Depressing Coloration or Decomposition of Kojic Acid

Lotion type samples and cream type samples were prepared as typical samples for the test.
1) Lotion type samples
Method of experiments:

Various lotions were prepared according to the formulations shown in Table 1. After placing them in 4-ounce candle bottle, they were wrapped with aluminum foil to cut light. These were kept at 45° C. for 30 days in a thermostatic chamber, and color difference (ΔE) was measured every 10 days (using a color-difference meter, MINOLTA CT-210).

TABLE 1

| | Tested samples | | | | |
|---|---|---|---|---|---|
| Formulation No. | Kind of Surfactant (amount: $4.2 \times 10^{-4}$ mol) | Kojic Acid g | Ethanol (ml) | Purified Water (ml) | HLB Value |
| 1 | Polyethylene glycol monostearate (55 EO) | | | To make the total 100 (pH: adjusted to 4.5) Citric | 18.0 |
| 2 | Polyethylene glycol monostearate (25 EO) | | | | 15.0 |
| 3 | Polyethylene glycol monostearate (10 EO) | | | | 11.0 |

TABLE 1-continued

| Formulation No. | Kind of Surfactant (amount: $4.2 \times 10^{-4}$ mol) | Kojic Acid g | Ethanol (ml) | Purified Water (ml) | HLB Value |
|---|---|---|---|---|---|
| 4 | Polyethylene glycol monostearate (4 EO) | 1.0 | 10 | acid (pH-adjusting agent) | 6.7 |
| 5 | POE(20)sorbitan monolaurate | | | | 16.9 |
| 6 | POE(20)sorbitan monopalmitate | | | | 15.6 |
| 7 | POE(20)sorbitan monostearate | | | | 14.9 |
| 8 | POE(6)sorbitan monostearate | | | | 9.6 |

Figure 2:
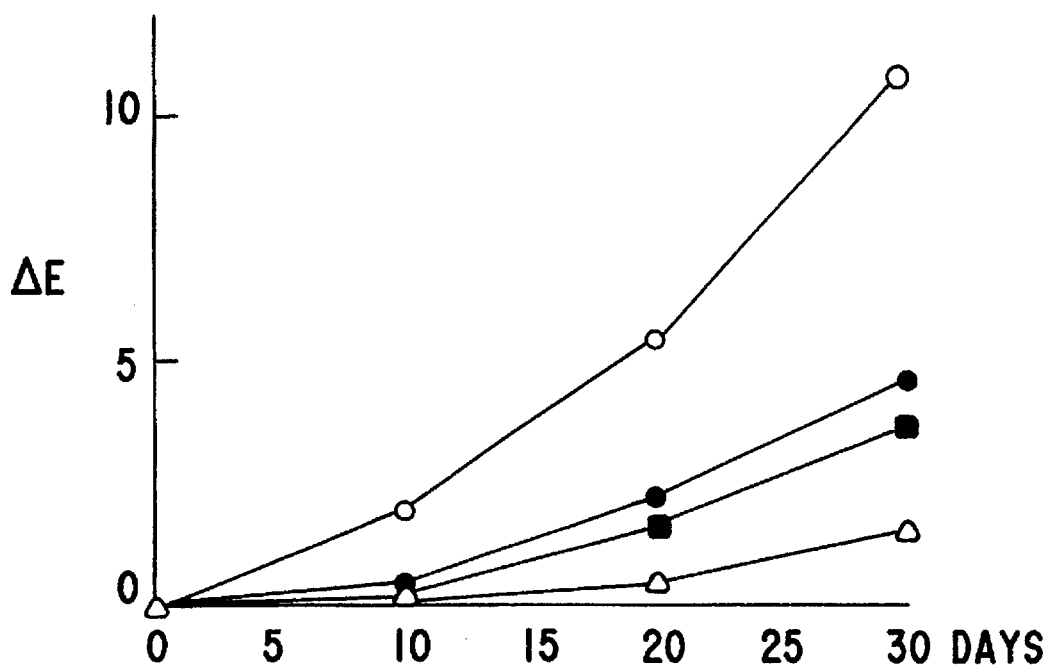
FIG. 2 is a graph showing change in coloration with time (ΔE) at 45° C. of a simple lotion of 4.5 in pH containing 1% of kojic acid, with differently changing HLB value of a surfactant.

Results of the experiment:

FIGS. 1 and 2 show color change (ΔE) with time of aqueous solutions (simple lotion system of 4.5 in pH) containing 1% of kojic acid and having variously adjusted HLB values. As the surfactant, polyethylene glycol fatty acid esters and polyoxyethylene sorbitan fatty acid esters were used as typical surfactants. It is seen that surfactants with less HLB vaues caused less coloration or decomposition of kojic acid, with particularly remarkable effect being obtained when the HLB value was up to 12.

2) Cream type samples

Method of experiments:

Various cream samples were prepared according to the formulations shown in Table 2. After placing them in 4-ounce candle bottle, they were wrapped with aluminum foil to cut light. These were kept at 45° C. for 30 days in a thermostatic chamber, and color difference (ΔE) was measured every 10 days (using a color-difference meter, Z-1001DP, made by Nihon Denshoku Kogyo).

TABLE 2

| | Tested samples | | | | |
|---|---|---|---|---|---|
| | O/W Preparation | | | W/O Preparation | |
| Ingredient | Formulation 1 | Formulation 2 | Formulation 3 | Formulation 4 | Formulation 5* |
| 1. Polyoxyethylene cetyl ether (25 EO) | 3.00 | — | — | — | — |
| 2. Oleophilic glycerol stearate | 1.50 | — | — | — | — |
| 3. Polyoxyethylene sorbitan monolaurate (20 EO) | — | 2.00 | — | — | — |
| 4. Oleophilic glycerol monooleate | — | 2.00 | — | 3.50 | — |
| 5. Polyethylene glycol (40 EO) monostearate | — | — | 2.00 | — | — |
| 6. Self-emulsifiable glycerol stearate | — | — | 5.00 | — | — |
| 7. Polyoxyethylene sorbitan monooleate ester (20 EO) | — | — | — | 1.00 | — |
| 8. Dimethylsiloxane methyl-(polyoxyethylene-polyoxypropylene) copolymer | — | — | — | — | 3.00 |
| 9. Microcrystalline wax | — | — | — | 9.00 | — |
| 10. Paraffin | — | — | — | 2.00 | — |
| 11. Vaseline | — | — | — | 5.00 | — |
| 12. Bees wax | — | 6.00 | — | 3.00 | — |
| 13. Reduced lanolin | 2.00 | 8.00 | — | 8.00 | — |
| 14. Cetanol | — | 5.00 | — | — | — |
| 15. Stearyl alcohol | 7.00 | — | — | — | — |
| 16. Behenyl alcohol | — | — | 1.00 | — | — |
| 17. Octyldodecanol | 6.00 | — | — | — | — |
| 18. Stearic acid | 2.00 | — | 5.00 | — | — |
| 19. Squalane | 5.00 | 37.50 | — | 34.00 | 5.00 |
| 20. Liquid paraffin | — | — | 10.00 | — | — |
| 21. Glyceryl trioctanoate | — | — | 10.00 | — | 3.00 |
| 22. Fatty acid glyceride | — | 4.00 | — | — | — |
| 23. Hexadecyl adipate ester | — | — | — | 10.00 | — |
| 24. Sucrose fatty acid ester | — | — | — | — | 0.20 |
| 25. Propylene glycol | 5.00 | 5.00 | 5.00 | 2.00 | — |
| 26. Glycerol | — | — | — | — | 12.00 |
| 27. Decamethylcyclopentasiloxane | — | — | — | — | 3.00 |
| 28. Octamethylcyclotetrasiloxane | — | — | — | — | 3.00 |
| 29. Dimethylpolysiloxane | — | — | — | — | 5.00 |
| 30. Kojic acid | 1.00 | 1.00 | 1.00 | 1.00 | 1.00 |
| 31. Purified water | *1 | *1 | *1 | *1 | *1 |
| HLB value of surfactants | 13.70 | 10.45 | 9.29 | 5.28 | 6.33 |

5*: Gel emulsion
*1: enough amount to make the total amount 100.00

Figure 3:
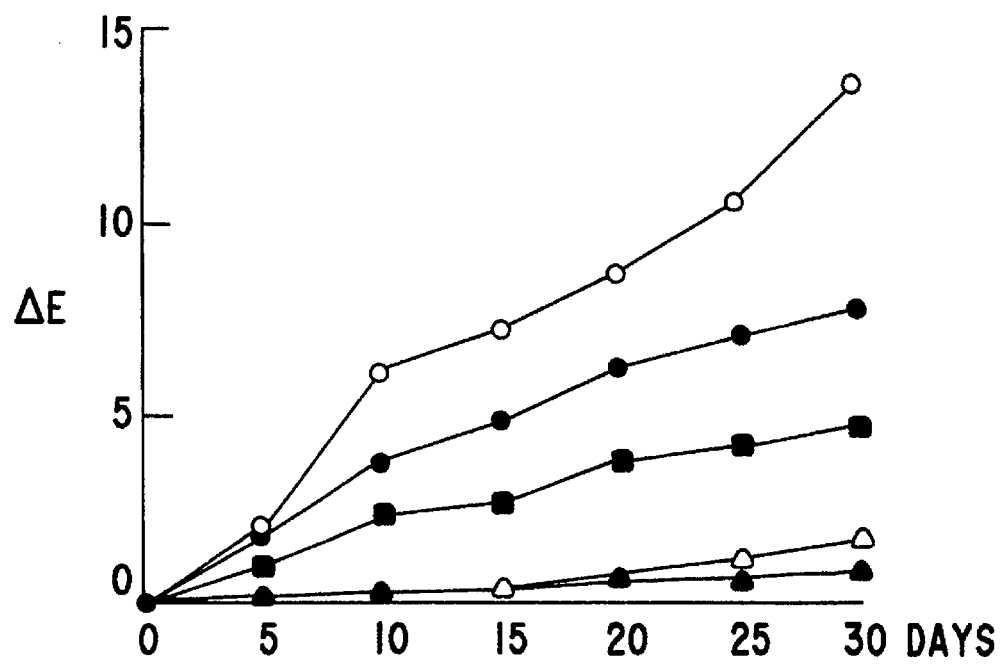
FIG. 3 is a graph showing change in coloration with time (ΔE) of a cream of 4.5 in pH containing 1% of kojic acid.

Results of the experiment:

FIG. 3 shows color change (ΔE) with time of cream samples containing 1% of kojic acid. It is seen that surfactants with less HLB vaues caused less coloration or decomposition of kojic acid in both O/W preparations and W/O preparations. W/O Preparations tend to suffer less coloration or decomposition of kojic acid in comparison with O/W preparations. It is apparent that the tendency is enhanced by utilizing the gel emulsification process.

EXPERIMENT 2

Application Test

The following organoleptic examination was conducted for examining application feel of the preparation of the present invention for epidermis.

Method of experiment:

Penetration feel to skin (fitness to skin), covering feel, sticky feel and wet feel of the W/O cream samples obtained in a general manner and the W/O cream samples obtained accordin to the gel emulsification process and shown in Table 3 were examined by 20 female special panelers according to the following standard. results thus obtained are shown in Table 4.

TABLE 3

Tested samples

| Ingredients | W/O Preparation of general type (%) | W/O Preparation of gel emulsification type (%) |
|---|---|---|
| 1. Oleophilic glycerol monooleate | 3.50 | — |
| 2. Polyoxyethylenesorbitan Monooleate ester (20 EO) | 1.00 | — |
| 3. Dimethylsiloxane methyl-(polyoxyethylene polyoxypropylene) copolymer | — | 3.00 |
| 4. Microcrystalline wax | 9.00 | — |
| 5. Paraffin | 2.00 | — |
| 6. Vaseline | 5.00 | — |
| 7. Bees wax | 3.00 | — |
| 8. Reduced lanolin | 8.00 | — |
| 9. Squalane | 34.00 | 5.00 |
| 10. Glyceryl trioctanoate | — | 3.00 |
| 11. Hexadecyl adipate ester | 10.00 | — |
| 12. Sucrose fatty acid ester | — | 0.20 |
| 13. Propylene glycol | 2.00 | — |
| 14. Glycerol | — | 12.00 |
| 15. Decamethylcyclopentasiloxane | — | 3.00 |
| 16. Octamethylcyclotetrasiloxane | — | 3.00 |
| 17. Dimethylpolysiloxane | — | 5.00 |
| 18. Kojic acid | 1.00 | 1.00 |
| 19. Purified water | *1 | *1 |

*1: enough amount to make the total 100.00

Standard for the examination:

⊙: 15 or more panelers out of 20 judged good.
Δ: 10 or more panelers out of 20 judged good.
X: 5 or less panelers out of 20 judged good.

Results of the experiment:

As can be seen from Table 4, W/O creams of the present invention obtained by the gel emulsification process show good application feel.

TABLE 4

Results of the organoleptic examination

| Item of Organoleptic Examination | W/O Preparation of General type | W/O Preparation obtained by Gel Emulsification |
|---|---|---|
| 1. Penetration feel into skin (fitness) | X | ⊙ |
| 2. Covering feel | X | Δ |
| 3. Sticky feel | X | ⊙ |
| 4. Wet feel | ⊙ | ⊙ |

FORMULATION EXAMPLE 1

W/O Cream

| | | (% by weight) |
|---|---|---|
| A | 1. Dimethylsiloxane methyl(polyoxyethylene/polyoxypropylene) copolymer | 3.00 |
| | 2. Diglyceryl monooleate | 1.00 |
| | 3. Sorbitan monostearate | 0.20 |
| B | 4. Squalane | 5.00 |
| | 5. glycerol trioctanoate | 3.00 |
| | 6. Natural vitamin E | 0.04 |
| | 7. 4-tert-Butyl-4'-methoxy-dibenzoyl-methane | 0.50 |
| C | 8. Glycerol | 10.00 |
| | 9. Sorbitol | 2.00 |
| | 10. Decamethylcyclopentasiloxane | 3.00 |
| | 11. Octamethylcyclotetrasiloxane | 3.00 |
| | 12. Dimethylpolysiloxane | 5.00 |
| | 13. Disodium edetate | 0.01 |
| | 14. Kojic acid | 5.00 |
| | 15. Purified water to make | 100.00 |

FORMULATION EXAMPLE 2

O/W Cream

| | | (% by weight) |
|---|---|---|
| A | 1. Polyoxyethylene cetyl ether (25 EO) | 2.50 |
| | 2. Oleophilic glycerol monostearate | 2.50 |
| | 3. Reduced lanolin | 2.00 |
| | 4. Stearic acid | 2.00 |
| | 5. Stearyl alcohol | 7.00 |
| | 6. Octyl dodecanol | 6.00 |
| | 7. Squalane | 5.00 |
| | 8. Natural vitamin E | 0.04 |
| | 9. Oxybenzonesulfonic acid | 0.50 |
| | 10. p-Hydroxybenzoic acid ester | 0.20 |
| B | 11. Propylene glycol | 5.00 |
| | 12. Disodium edetate | 0.01 |
| | 13. Kojic acid | 3.00 |
| | 14. Purified water to make | 100.00 |

FORMULATION EXAMPLE 3

O/W Emulsion

|   |   |   | (% by weight) |
|---|---|---|---|
| A | 1. | Polyoxyethylene sorbitan monostearate (20 EO) | 2.00 |
|   | 2. | Polyoxyethylene sorbitol tetraoleate (60 EO) | 0.50 |
|   | 3. | Oleophilic glyceryl monostearate | 1.00 |
|   | 4. | Stearic acid | 0.50 |
|   | 5. | Behenyl alcohol | 0.50 |
|   | 6. | Avocado oil | 4.00 |
|   | 7. | Glyceryl trioctanoate | 4.00 |
|   | 8. | Natural vitamin E | 0.04 |
|   | 9. | Ethylene glycol salicylate | 0.10 |
|   | 10. | p-Hydroxybenzoic acid ester | 0.20 |
| B | 11. | 1,3-butylene glycol | 5.00 |
|   | 12. | Xanthane gum | 0.14 |
|   | 13. | Disodium edetate | 0.01 |
|   | 14. | Kojic acid | 0.50 |
|   | 15. | Purified water to make | 100.00 |

FORMULATION EXAMPLE 4

O/W Cream Pack

|   |   |   | (% by weight) |
|---|---|---|---|
| A | 1. | Polyethylene glycol monostearate (40 EO) | 2.00 |
|   | 2. | Self-emulsifiable glycerol monostearate | 5.00 |
|   | 3. | Stearic acid | 5.00 |
|   | 4. | Behenyl alcohol | 0.50 |
|   | 5. | Squalane | 15.00 |
|   | 6. | Cetyl octanoate | 5.00 |
|   | 7. | Natural vitamin E | 0.04 |
|   | 8. | 4-tert-Butyl-4'-methoxy-dibenzoyl-methane | 0.50 |
|   | 9. | p-Hydroxybenzoic acid ester | 0.20 |
| B | 10. | 1,3-Butylene glycol | 5.00 |
|   | 11. | Disodium edetate | 0.01 |
|   | 12. | Kojic acid glucoside | 2.00 |
|   | 13. | Purified water to make | 100.00 |

FORMULATION EXAMPLE 5

O/W Essence

|   |   |   | (% by weight) |
|---|---|---|---|
| A | 1. | Polyoxyethylene sorbitan monostearate (20 EO) | 1.00 |
|   | 2. | Polyoxyethylene sorbitol tetraoleate (60 EO) | 0.50 |
|   | 3. | Oleophilic glyceryl monostearate | 1.00 |
|   | 4. | Stearic acid | 0.50 |
|   | 5. | Behenyl alcohol | 0.50 |
|   | 6. | Avocado oil | 2.00 |
|   | 7. | Squalane | 3.00 |
|   | 8. | Glyceryl trioctanoate | 3.00 |
|   | 9. | Natural vitamin E | 0.04 |
|   | 10. | Oxybenzone | 0.50 |
|   | 11. | p-Hydroxybenzoic acid ester | 0.20 |
| B | 12. | 1,3-butylene glycol | 5.00 |
|   | 13. | Xanthane gum | 0.14 |
|   | 14. | Disodium edetate | 0.10 |
|   | 15. | Kojic acid | 1.00 |
|   | 16. | Purified water to make | 100.00 |

It has been confirmed that the above-described formulation Examples 1 to 5 providepreparations having the same satisfactory results.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A method of preventing the discoloration and decomposition of kojic acid in a topically administrable, oil-in-water or water-in-oil emulsion comprising a) 0.1–5% by weight of kojic acid, b) 5–50%, based on the weight of the oil in the emulsion, of at least one nonionic surfactant and c) water to 100% of the emulsion; which comprises adjusting the HLB value of the at least one surfactant to 12 or below.

2. A method according to claim 1 wherein the least one nonionic surfactant is selected from the group consisting of sorbitan fatty acid esters, glycerol fatty acid esters, polyoxyethylene sorbitol fatty acid esters, polyoxyethylene glycol fatty acid esters, polyoxyethylene alkyl ethers, polyoxyethylene alkylphenyl ethers, polyoxyethylene fats and oils, polyoxyethylene alkyl ether phosphates, propylene glycol fatty acid esters, polyoxyethylene polyoxypropyrene glycol ethers and saccharose fatty acid esters.

* * * * *